United States Patent
Vignon et al.

(10) Patent No.: US 11,087,466 B2
(45) Date of Patent: Aug. 10, 2021

(54) METHODS AND SYSTEM FOR COMPOUND ULTRASOUND IMAGE GENERATION

(71) Applicant: KONINKLIJKE PHILIPS N.V., Eindhoven (NL)

(72) Inventors: Francois Guy Gerard Marie Vignon, Andover, MA (US); William Hou, Briarcliff Manor, NY (US); Jean-Luc Francois-Marie Robert, Cambridge, MA (US); Emil George Radulescu, Ossining, NY (US); Ji Cao, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/622,375

(22) PCT Filed: Jun. 18, 2018

(86) PCT No.: PCT/EP2018/066053
§ 371 (c)(1),
(2) Date: Dec. 13, 2019

(87) PCT Pub. No.: WO2018/234209
PCT Pub. Date: Dec. 27, 2018

(65) Prior Publication Data
US 2020/0202518 A1    Jun. 25, 2020

Related U.S. Application Data

(60) Provisional application No. 62/523,318, filed on Jun. 22, 2017.

(51) Int. Cl.
*A61B 8/00* (2006.01)
*G06T 7/00* (2017.01)
(Continued)

(52) U.S. Cl.
CPC .......... *G06T 7/0012* (2013.01); *A61B 8/4245* (2013.01); *G06T 5/50* (2013.01);
(Continued)

(58) Field of Classification Search
CPC ........... G06T 7/0012; G06T 7/73; G06T 5/50; G06T 2207/10132; G06T 2207/20182;
(Continued)

(56) References Cited

U.S. PATENT DOCUMENTS 6,126,598 A  10/2000  Entrekin et al.
6,547,732 B2  4/2003  Jago
(Continued)

FOREIGN PATENT DOCUMENTS

WO    2015087227 A1    6/2015

OTHER PUBLICATIONS

Vincent Grau and J. Alison Noble "Adaptive Multiscale Compounding Using Phase Information", Oct. 26-29, 2005, Medical Image Computing and Computer-Assisted Intervention—MICCAI 2005, 8th International conference, pp. 589-596. (Year: 2005).*
(Continued)

*Primary Examiner* — Siamak Harandi

(57) ABSTRACT

The invention provides a method for generating a compound ultrasound image. The method includes acquiring and beamforming channel data. Using the beamformed channel data a plurality of images, each image comprising a plurality of pixels, of a region of interest are obtained and an image information metric, wherein the image metric is associated with a pixel of the plurality of pixels, is assessed. The acquiring of the plurality of images and the assessment of the image metric are performed in parallel. For each image of the plurality of images: a per-pixel weighting for each pixel of the plurality of pixels based on the assessment of the image information metric is determined and applied to each
(Continued)

pixel of the plurality of pixels. Finally a compound ultrasound image is generated based on the plurality of weighted pixels of the plurality of images.

18 Claims, 5 Drawing Sheets

(51) Int. Cl.
  *G06T 7/73* (2017.01)
  *G06T 5/50* (2006.01)
(52) U.S. Cl.
  CPC ...... *G06T 7/73* (2017.01); *G06T 2207/10132* (2013.01); *G06T 2207/20182* (2013.01); *G06T 2207/20221* (2013.01); *G06T 2207/30004* (2013.01)
(58) Field of Classification Search
  CPC . G06T 2207/20221; G06T 2207/30004; A61B 8/4245
  See application file for complete search history.

(56) References Cited

U.S. PATENT DOCUMENTS

2008/0306382 A1    12/2008  Guracar et al.
2017/0301094 A1*   10/2017  Vignon ..................... G06T 5/20
2019/0369240 A1*   12/2019  Gan ....................... A61B 8/5276

OTHER PUBLICATIONS

International Search Report and Written Opinion for International Application Serial No. PCT/EP2018/066053, filed Jun. 18, 2018, 13 pages.
Entrekin, et al., "Real Time Spatial Compound Imaging in breast ultrasound: technology and early clinical experience", Medicamundi, vol. 43, Issue 3, Sep. 1999, pp. 35-43.
Tran, et al., "Adaptive Spatial compounding for improving ultrasound images of the epidural space", Medical Imaging 2007, Ultrasonic Imaging and Signal Processing, Proc. of SPIE, vol. 6513, pp. 65130W-1 to 65130W-12.
Cheung, et al., "Enhancement of Needle Visibility in Ultrasound-Guided Percutaneous Procedures", Ultrasound in Med. & Biol., vol. 30, No. 5, pp. 617-624.
Zhuang, et al., "Adaptive Spatial Compounding for Needle Visualization", 2011 IEEE International, Ultrasonics Symposium, 4 pages.
Rajpoot, et al., "Multiview Fusion 3-D Echocardiography: Improving the Information and Quality of Real-Time 3-D Echocardiography", Ultrasound in Med. & Biol. vol. 37, No. 7, pp. 1056-1072.

* cited by examiner $$CF(m, rx) \equiv \frac{\sum_{tx=rx-\Delta}^{rx+\Delta} \left| \sum_{n=1}^{N} S(m, n, tx, rx) \right|^2}{\sum_{tx=rx-\Delta}^{rx+\Delta} N \sum_{n=1}^{N} \left| S(m, n, tx, rx) \right|^2} \quad \text{(definition 1)}$$

204, 208, 206

$$R(m, rx) \equiv \frac{1}{2d+1} \sum_{p=m-d}^{m+d} s(p, rx) s^H(p, rx) \quad \text{(definition 2)}$$

210, 214 where $$s(p, rx) = \begin{bmatrix} S(p, 1, rx, rx) \\ S(p, 2, rx, rx) \\ \vdots \\ S(p, N, rx, rx) \end{bmatrix} \quad \text{(definition 3)}$$

$$Tr\{R(m, rx)\} \equiv \sum_{i=1}^{N} R_{ii}(m, rx) = \sum_{i=1}^{N} \gamma_{ii}(m, rx) \quad \text{(definition 4)}$$

212

$$ev_d(m, rx) \equiv \frac{1}{1 - \frac{\gamma_1(m, rx)}{Tr\{R(m, rx)\}}} \quad \text{(definition 5)}$$

216, 218

$$R(m, rx) \equiv \frac{1}{(2d+1)(2g+1)} \sum_{p=m-d}^{m+d} \sum_{tx=rx-g}^{rx+g} s(p, tx, rx) s^H(p, tx, rx)$$

(definition 6)

where $$s(p, tx, rx) = \begin{bmatrix} S(p, 1, tx, rx) \\ S(p, 2, tx, rx) \\ \vdots \\ S(p, N, tx, rx) \end{bmatrix} \quad \text{(definition 7)}$$

FIG. 2

METHODS AND SYSTEM FOR COMPOUND ULTRASOUND IMAGE GENERATION

RELATED APPLICATIONS

This application is the U.S. National Phase application under 35 U.S.C. § 371 of International Application No. PCT/EP2018/066053, filed on Jun. 18, 2018, which claims the benefit of and priority to U.S. Provisional No. 62/523,318, filed Jun. 15, 2017. These applications are hereby incorporated in their entirety by reference herein.

RELATED APPLICATION

This application claims the benefit of and priority to U.S. Provisional Application No. 62/523,318, filed Jun. 22, 2017, which is incorporated by reference in its entirety.

FIELD OF THE INVENTION

This invention relates to ultrasound imaging and, more particularly, to generating a compound ultrasound image.

BACKGROUND OF THE INVENTION

In general, generating a compound image in an ultrasound system consists of imaging the same medium with different insonation parameters and averaging the resulting views.

For example, in the case of spatial compounding the medium is imaged at various viewing angles, each generating a different view. The views are then averaged to generate the compound ultrasound image. This results in decreased speckle variance and increased visibility of plate-like scatterers (boundaries) along with other image quality improvements. The averaging reduces speckle noise and improves image quality because they depict similar anatomical features, despite the views having different noise patterns. In addition, certain structures that are only visible, or more visible, at certain imaging angles, may be enhanced through spatial compounding.

The speed of sound varies by as much as 14% in soft tissue, meaning that a slight positioning mismatch of structures may be present in the different views. In this case, the compounding may lead to blurring. In addition, the compounding may lead to: the sidelobes of the point-spread functions at different view angles being averaged, resulting in increased smearing of tissue in cysts; grating lobes from the different angled views corrupting the compound ultrasound image; and structures that are only visible at a given angle not being sufficiently enhanced because the optimal view is averaged with other, sub-optimal views. These combined effects result in a decreased contrast of the compounded ultrasound image compared to the single-view images.

SUMMARY OF THE INVENTION

The present invention provides systems and methods for generating a compound ultrasound image whilst maintaining image contrast without requiring significant additional hardware.

According to examples in accordance with an aspect of the invention, there is provided a method for generating a compound ultrasound image, the method comprising:
  acquiring channel data;
  beamforming the channel data;
  in parallel, using the beamformed channel data to:
    obtain a plurality of images, each image comprising a plurality of pixels, of a region of interest; and
    assess an image information metric for each pixel of a plurality of images; and
  for each image of the plurality of images:
    determining a per-pixel weighting for each pixel of the plurality of pixels based on the assessment of the image information metric; and
    applying the per-pixel weighting to each pixel of the plurality of pixels; and
  generating a compound ultrasound image based on the plurality of weighted pixels of the plurality of images.

This method generates a compound ultrasound image from a plurality of weighted ultrasound images. In this way, it is possible to generate a compound ultrasound image where the key features are preferentially weighted based on a predetermined image metric. By performing the image acquisition and image metric assessment in parallel, it is possible to significantly increase the efficiency of the method and reduce the time required to generate the compound ultrasound image. In addition, as the beamformed channel data typically contains more detail than the conventional B-mode ultrasound image, the image metric assessment based on the beamformed channel data may be more accurate than an assessment based on the image itself, thereby increasing the accuracy of the weightings, and so the compound ultrasound image.

The pixels of the compound ultrasound image may be thought of as a weighted average of the pixels of the plurality of images obtained from the beamformed channel data.

In an embodiment, the plurality of pixels are volumetric pixels.

In this way, it is possible to generate a three dimensional compound ultrasound image.

In an arrangement, each image of the plurality of images comprises a viewing angle of the region of interest, wherein the viewing angle of each image is different.

In this way, it is possible for the images to provide uncorrelated content from each view, meaning that anisotropic features appearing under only a few viewing angles are more likely to be captured in one of the plurality of images. By capturing these features in at least one of the plurality of images, the feature may be weighted to appear more clearly in the compound ultrasound image, thereby increasing the accuracy of the final image.

In some arrangements, the image metric comprises at least one of a feature and an orientation.

In this way, it is possible to either identify a common feature or identify the changes in orientation between each of the images, which may then be used in the generation of the compound ultrasound image.

In some embodiments, the assessing of the image metric comprises assessing a coherence metric of the beamformed channel data.

In this way, it is possible to distinguish between low coherence signals, such as system noise, high coherence signals, such as signals from a point scatterer, and intermediate coherence signals, such as speckle. In this way, the coherence metric may be used to apply appropriate weightings to minimize noise and highlight important features in the region of interest.

In an embodiment, the coherence metric comprises at least one of: a coherence factor; a dominance of an eigenvalue of a covariance matrix; and a Wiener factor.

In some embodiments, the generation of the compound ultrasound image comprises performing at least one of: spatial; temporal; or frequency compounding on the weighted pixels.

In this way, it is possible to compound images obtained from: different viewing angles; independent acoustic windows; and different imaging frequencies, respectively.

In an arrangement, the generation of the compound ultrasound image comprises at least one of retrospective dynamic transmit (RDT) focusing and incoherent RDT focusing.

In some arrangements, the generation of the compound ultrasound image is performed in a multi-scale fashion.

In this way, it is possible to separate the image data based on the spatial frequencies of the image. By separating the image data by spatial frequencies, low spatial frequency signals, which may contain structures such as cysts, may be used in the image metric assessment, whilst high spatial frequency signals, which may contain speckle, may be discarded.

In an embodiment, the method further comprises assigning brightness values to the plurality of pixels of each image based on the assessment of the image metric.

In this way, it is possible to generate a visual representation of the beamformed channel data assessment. In addition, in the case where more than one image metric is used, the brightness value may provide a simple representation of multiple complex parameters.

In a further embodiment, the determining of the weighting for each pixel is based on at least one of a maximum brightness value; a mean brightness value; and a minimum brightness value of the plurality of pixels across the plurality of images.

In this way, the maximum brightness value pixels may be weighted highly for important features of the region of interest, minimum brightness value pixels may be weighted highly in areas of high system noise, thereby removing clutter from the compound ultrasound image, and mean brightness value pixels may be weighted highly in areas of speckle signals.

In a yet further embodiment, the method further comprises:
generating a mean brightness value image based on the mean brightness value of the plurality of pixels across the plurality of images;
subtracting the mean brightness value image from the compound ultrasound image, thereby generating a difference image;
applying a low pass filter to the difference image; and
summing the mean brightness value image and the subtraction image, thereby generating a speckle filtered compound ultrasound image.

In this way, it is possible eliminate speckle artifacts from the compound ultrasound image.

According to examples in accordance with an aspect of the invention, there is provided a computer program comprising computer program code means which is adapted, when said computer program is run on a computer, to implement the method described above.

According to examples in accordance with an aspect of the invention, there is provided a system for generating a compound ultrasound image, the system comprising:
an ultrasonic probe, adapted to acquire channel data;
a beamforming module, adapted to apply beamforming to the channel data;
a controller adapted to:
in parallel, use the beamformed channel data to:
obtain a plurality of images, each image comprising a plurality of pixels, of a region of interest; and
assess an image information metric for each pixel of a plurality of images; and
for each image of the plurality of images:
determine a per-pixel weighting for each pixel of the plurality of pixels based on the assessment of the image information metric; and
apply the per-pixel weighting to each pixel of the plurality of pixels; and
a pixel compounder, adapted to generate a compound ultrasound image based on the plurality of weighted pixels of the plurality of images.

In an embodiment, the ultrasonic probe comprises an electronic steering unit adapted to alter the viewing angle of the ultrasonic probe.

BRIEF DESCRIPTION OF THE DRAWINGS

Examples of the invention will now be described in detail with reference to the accompanying drawings, in which:
FIG. 2 shows a set of mathematical definitions and relationships.

DETAILED DESCRIPTION OF THE EMBODIMENTS

The invention provides a method for generating a compound ultrasound image. The method includes acquiring and beamforming channel data. Using the beamformed channel data a plurality of images, each image comprising a plurality of pixels, of a region of interest are obtained and an image information metric, wherein the image metric is associated with a pixel of the plurality of pixels, is assessed. The acquiring of the plurality of images and the assessment of the image metric are performed in parallel. For each image of the plurality of images: a per-pixel weighting for each pixel of the plurality of pixels based on the assessment of the image information metric is determined and applied to each pixel of the plurality of pixels. Finally a compound ultrasound image is generated based on the plurality of weighted pixels of the plurality of images.

Figure 1:
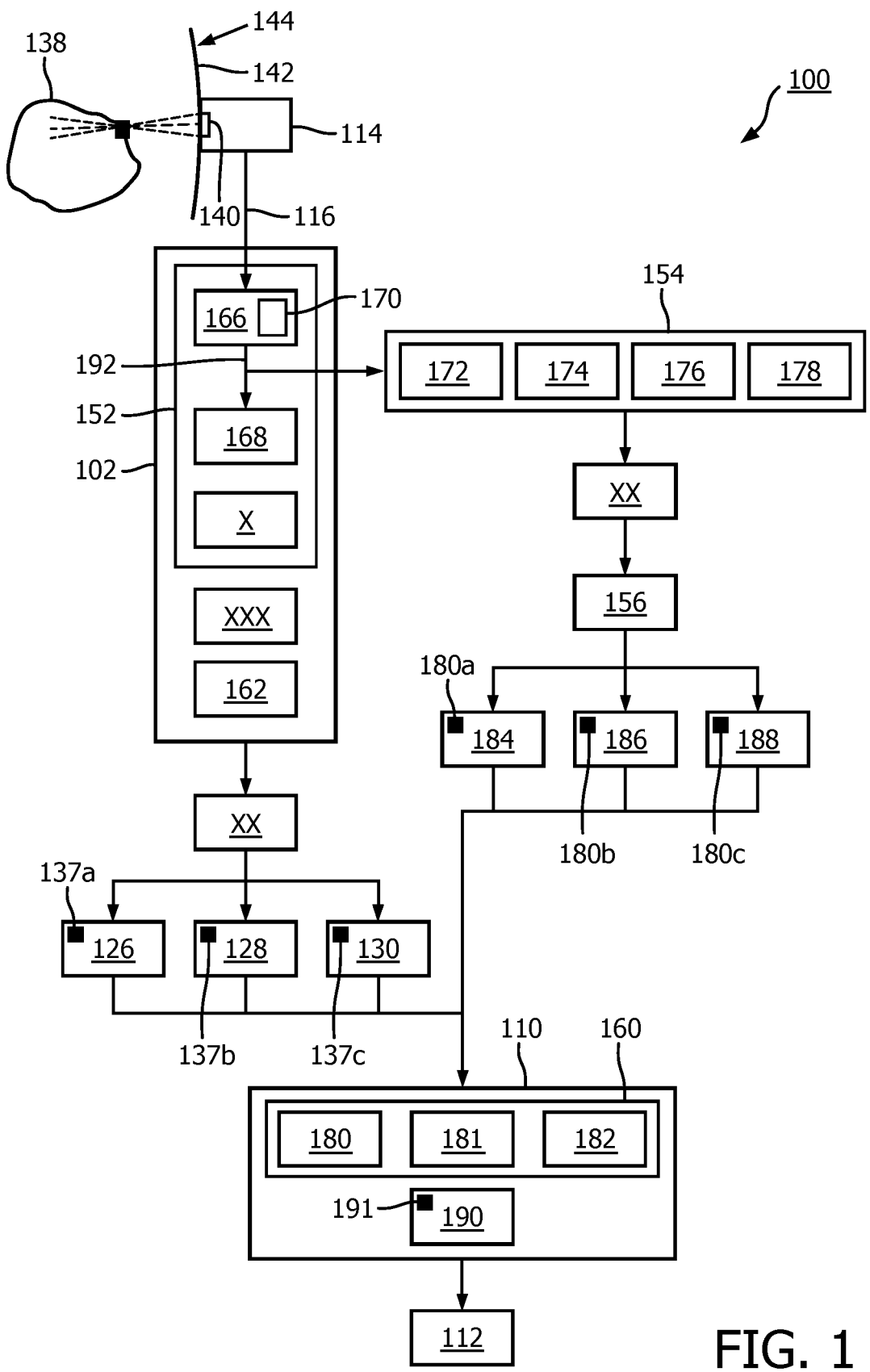
FIG. 1 shows a schematic diagram of a compound ultrasound imaging system.

FIG. 1 is a schematic representation of an ultrasound system 100 adapted to generate compound ultrasound images. The system includes an ultrasound probe 114 connected by a cable 116 to an image formation module 102. The image formation module contains a channel beamformer 166 and a beamspace beamformer X. The apparatus further comprises an image content assessment module 154, a weight determination module 156, an image processor 110, and an imaging display 112.

The imaging probe 114 is used to perform several observations of the medium of interest 138 under different conditions, such as varying transmit/receive angle or transmit/receive frequency. For example, three transmit angles may be used to produce three respective images 126, 128, 130. The images may vary in transmit or receive angle or both, in the case of spatial compounding, or in transmit or receive frequency or both in the case of frequency compounding, or in both angle and frequency.

A scan conversion and spatial registration module XX ensures that all images are spatially registered, meaning that each pixel 137 of an image spatially corresponds to a pixel of each of the remaining images, and spatially corresponds to a pixel of the final compound ultrasound image 190 to be formed. The images may be two-dimensional or three-dimensional.

In this case, the different images 126, 128, 130 of a region of interest 138 are obtained from a single, acoustic window 140 on an outer surface 142, or skin, of an imaging subject 144, such as a human patient or animal. Alternatively, or in addition, more than one acoustic window on the outer surface 142 may be utilized for acquiring views having different angles. The probe 114 may be moved from window to window, or additional probes may be placed at each acoustic window. In the case of multiple acoustic windows, temporal compounding may be performed on the multiple images.

The image formation module 102 comprises a beamforming module 152. The beamforming module 152 contains an electronic steering module, also referred to as a channel beamformer 166, and a beamforming summation module 168. The electronic steering module 166 includes a beamforming delay module 170 adapted to introduce a delay to various channel data signals. The beamforming module 152 may also comprise a beamspace beamforming module X. The image formation module 102 further comprises an envelope detection module XXX and a logarithmic compression module 162.

The image content assessment module 154 may include a classifier module 172, a coherence factor module 174, a covariance matrix analysis module 176, and a Wiener factor module 178. In some cases, the image content assessment module may further include other modules to measure local coherence of signals by way of alternative coherence metrics.

The image processor 110 includes a pixel compounder 160. The pixel compounder 160 includes a spatial compounder 180, a temporal compounder 181, and a frequency compounder 182. Inputs to the pixel compounder 160 include pixels 137a, 137b, 137c, of the three images 126, 128, 130, that spatially correspond to the current pixel of the compound image 191 to be formed, i.e., the current compound image pixel. These inputs are accompanied by weighting inputs 180a, 180b and 180c from respective weighting images 184, 186, 188 determined by the weight determination module 156. The output of the pixel compounder 160 is a compound pixel 191 of the compound ultrasound image 190 being formed.

The operational principles of the coherence factor module 174 and covariance matrix analysis module 176 are described below.

With regard to coherence estimation, as performed by the coherence factor module 174, let S(m, n, tx, rx) denote complex RF, beamforming-delayed channel data 192, i.e. the beamformed channel data formed after the application of beamforming delays, by the channel beamformer 166, but before beamsumming, by the beamforming summation module 168. Here, m is the imaging depth/time counter or index, n the channel index, tx the transmit beam index, and rx the receive beam index. A coherence factor (CF) or "focusing criterion" at a pixel (m, rx), or field point, 137 with a single receive beam rx is calculated as follows:

$$CF_0(m, rx) \equiv \frac{\left|\frac{1}{N}\sum_{n=1}^{N} S(m, n, rx)\right|^2}{\frac{1}{N}\sum_{n=1}^{N} |S(m, n, rx)|^2},$$

where N is the number of channels.

In the case that multiple transmit beams are incorporated into the CF estimation; the CF formula may be redefined as:

$$CF(m, rx) \equiv \frac{\sum_{tx=rx-\Delta}^{rx+\Delta}\left|\sum_{n=1}^{N} S(m, n, tx, rx)\right|^2}{\sum_{tx=rx-\Delta}^{rx+\Delta} N \sum_{n=1}^{N} |S(m, n, tx, rx)|^2}, \quad \text{(definition 1)}$$

where $\Delta$ is a tunable parameter used to perform averaging over multiple transmit events in the case of coherent transmit compounding being used in the beamformer.

This definition, like the ones that follow, is repeated in FIG. 2. The assessing of an image metric with respect to pixel (m, rx) by computing CF(m, rx) is performed in parallel to the acquiring of the images 126, 128 and 130. In addition, the assessment of the delayed channel data 192 commences no later than the beamforming summation, i.e., the summation $\sum_{n=1}^{N} S(m, n, tx, rx)$.

As mentioned above, the pixel (m, rx) 137 is a function of position. The coherence estimation operates on the delayed channel data 192. The CF(m, rx) estimate, or result of the estimation, 204 may include summing, over multiple transmit beams, a squared-magnitude function 206 and a squared beamsum 208, which is the summed result of beamforming. The function 206 and beamsum 208 are both formed by summing over the channels of the channel data.

Referring now to the covariance matrix analysis, performed by the covariance matrix analysis module, let R(m, rx) denote a covariance matrix, or correlation matrix, 210 at the pixel (m, rx) obtained by temporal averaging over a range 214 of time or spatial depth:

$$R(m, rx) \equiv \frac{1}{2d+1}\sum_{p=m-d}^{m+d} s(p, rx)s^H(p, rx), \quad \text{(definition 2)}$$

where:

$$s(p, rx) = \begin{bmatrix} S(p, 1, rx) \\ S(p, 2, rx) \\ \vdots \\ S(p, N, rx) \end{bmatrix}, \quad \text{(definition 3)}$$

and $s^H$ is the Hermitian transpose of s. p indicates the depth sample index and d is a tunable parameter used to define a depth window over which the covariance is estimated. This may be of the order of the transmit pulse length, which is typically several wavelengths.

As R(m, rx) is a positive semidefinite matrix, all of its eigenvalues 212 are real and positive. Denoting the eigenvalues as $\{y_i(m, rx)\}_{i=1}^{N}$, with $y_i \geq y_{i+1}$, the trace of R(m, rx) may be written as:

$$Tr\{R(m,rx)\} = \sum_{i=1}^{N} R_{ii}(m,rx) = \sum_{i=1}^{N} y_i(m,rx). \quad \text{(definition 4)}$$

The dominance 216 of the first eigenvalue 218 is represented as:

$$ev_d(m, rx) \equiv \frac{1}{1 - \frac{\gamma_i(m, rx)}{Tr\{R(m, rx)\}}}. \qquad \text{(definition 5)}$$

The dominance is infinite if $y_i(m, rx)=0$ for $i \geq 2$, i.e. if the rank of R(m, rx) is 1, as $Tr\{R(m, rx)\}=y_1(m, rx)$, and finite otherwise. Summing over several transmits, also referred to as beam averaging, may also be applied in covariance matrix analysis as follows:

$$R(m, rx) \equiv \frac{1}{(2d+1)(2g+1)} \sum_{p=m-d}^{m+d} \sum_{tx=rx-\Delta}^{rx+\Delta} s(p, tx, rx) s^H(p, tx, rx), \qquad \text{(definition 6)}$$

where:

$$s(p, tx, rx) = \begin{bmatrix} S(p, 1, tx, rx) \\ S(p, 2, tx, rx) \\ \vdots \\ S(p, N, tx, rx) \end{bmatrix}. \qquad \text{(definition 7)}$$

Another way of combining transmits is to form the covariance matrix from data generated by an algorithm that recreates focused transmit beams retrospectively. An example utilizing RDT focusing is as follows, and, for other algorithms such as incoherent RDT, plane wave imaging and synthetic aperture beamforming, analogous eigenvalue dominance computations apply:

$$R(m, rx) \equiv \frac{1}{2d+1} \sum_{p=m-d}^{m+d} s_{RDT}(p, rx) s_{RDT}^H(p, rx),$$

where $$s_{RDT}(p, rx) = \begin{bmatrix} S_{RDT}(p, 1, rx) \\ S_{RDT}(p, 2, rx) \\ \vdots \\ S_{RDT}(p, N, rx) \end{bmatrix},$$

wherein, $S_{RDT}$ (p, n, rx) are the dynamically transmit-beamformed, complex RF channel data obtained by performing retrospective dynamic transmit (RDT) focusing on the original channel data S(m, n, tx, rx). As with the coherence factor assessment, the assessing of an image metric with respect to (m, rx) by computing R(m, rx) is performed in parallel to the acquiring of the images 126, 128 and 130. In addition, the assessment of the delayed channel data 192 commences no later than the beamforming summation.

In the above approach, $CF_0(m, rx)$ or CF(m, rx) may, as with the eigenvalue dominance, also be obtained by way of temporal averaging over a range 214 of time or spatial depth 140.

According to J. R. Robert and M. Fink, "Green's function estimation in speckle using the decomposition of the time reversal operator: Application to aberration correction in medical imaging," J. Acoust. Soc. Am., vol. 123, no. 2, pp. 866-877, 2008, the dominance of the first eigenvalue $ev_d$(m, rx) may be approximated by $1/(1-CF_1(m, rx))$, where $CF_1$(m, rx) is a coherence factor obtained from channel data S(m, n, tx, rx). Temporal averaging, averaging over multiple transmit beams and/or RDT may be applied in calculating $CF_1$(m, rx). Inversely, the coherence factor may be approximated based on the eigenvalue dominance derived with appropriate averaging.

In addition to the CF metric and eigenvalue dominance metric, another example of an image metric that may be used is the Wiener factor, which is applicable in the case of RDT and IRDT. The Wiener factor module 178 for deriving the Wiener factor operates on the following principles.

K ultrasound wavefronts (transmits) sequentially insonify the medium 138. The waves backscattered by the medium are recorded by the transducer array of the ultrasonic probe and beamformed in receive to focus on the same pixel 137. It is assumed here that the pixel is formed by RDT, or IRDT, focusing.

The result is a set of K receive vectors denoted as $r_i(P)$, where i=1, . . . , K, of size N samples (one sample per array element) that correspond to a signal contributing to pixel P 137. Each of the vectors can be seen as a different observation of the pixel 137. The entries of $r_i(P)$ are complex having both a non-zero real component and imaginary component.

Each of the receive vectors is weighted by the apodization vector a, which is for example a Box, Hanning, or Riesz window, and summed across the receive elements. This yields K beam-sum values that correspond to the Sample Values (SV) as obtained with the K different insonifications:

$$\{SV_1(P)=a^H r_1(P); SV_2(P)=a^H r_2(P); \ldots ; SV_K(P)=a^H r_K(P)\} \qquad \text{(expression 1)}$$

The collection of these K sample values is called the "RDT vector." Note that the RDT sample value is obtained by summing the values of the RDT vector as follows:

$$SV_{RDT}=\sum_{i=1}^{K} a^H r_K(P) \qquad \text{(expression 2)}$$

The Wiener factor is given as:

$$w_{wiener}(P) = \frac{\left|\sum_{i=1}^{K} a^H r_i(P)\right|^2}{\sum_{i=1}^{k} |a^H r_i(P)|^2} \qquad \text{(expression 3)}$$

The numerator of expression 3 is the square of the coherent sum of the elements of the RDT vector, i.e. the RDT sample value squared. The denominator is the incoherent sum of the squared elements of the RDT vector. In other words, if the incoherent RDT sample value ($SV_{IRDT}$) is defined as the square root of the numerator, then:

$$w_{wiener}(P) = \frac{|SV_{RDT}(P)|^2}{|SV_{IRDT}(P)|^2}$$

The Wiener factor is the ratio between the coherent RDT energy and the incoherent RDT energy. Thus, it may be considered as a coherence factor in beam space. It may be used as an image metric for RDT and IRDT focusing. Once again, the assessing of local image content with respect to pixel 137 by computing $w_{wiener}(P)$ is performed in parallel to the acquiring of the images 126, 128 and 130. In addition, the assessment of the delayed channel data 192 commences no later than the beamforming summation i.e. the summation $\Sigma_{i=1}^{K} a^H r_K(P)$.

Direct image metrics may also be used in lieu of the signal-based image metrics, such as coherence factor. For example, known confidence metrics in the literature are usually based on the local gradient and Laplacian of the image. See, for example, Frangi et al, "Multiscale vessel enhancement filtering", MICCAI 1998. A "confidence factor" may be computed from the pre-compressed data as follows: at each pixel, a rectangular box of approximately 20 by 1 pixels is rotated with the spatially corresponding pixel 180a-180c in the middle of the box. The box is rotated from 0 to 170 degrees by increments of 10 degrees. For each orientation of the box, the mean pixel values inside the box are recorded. The final metric is equal to the maximum of this metric across all angles.

Figure 3:
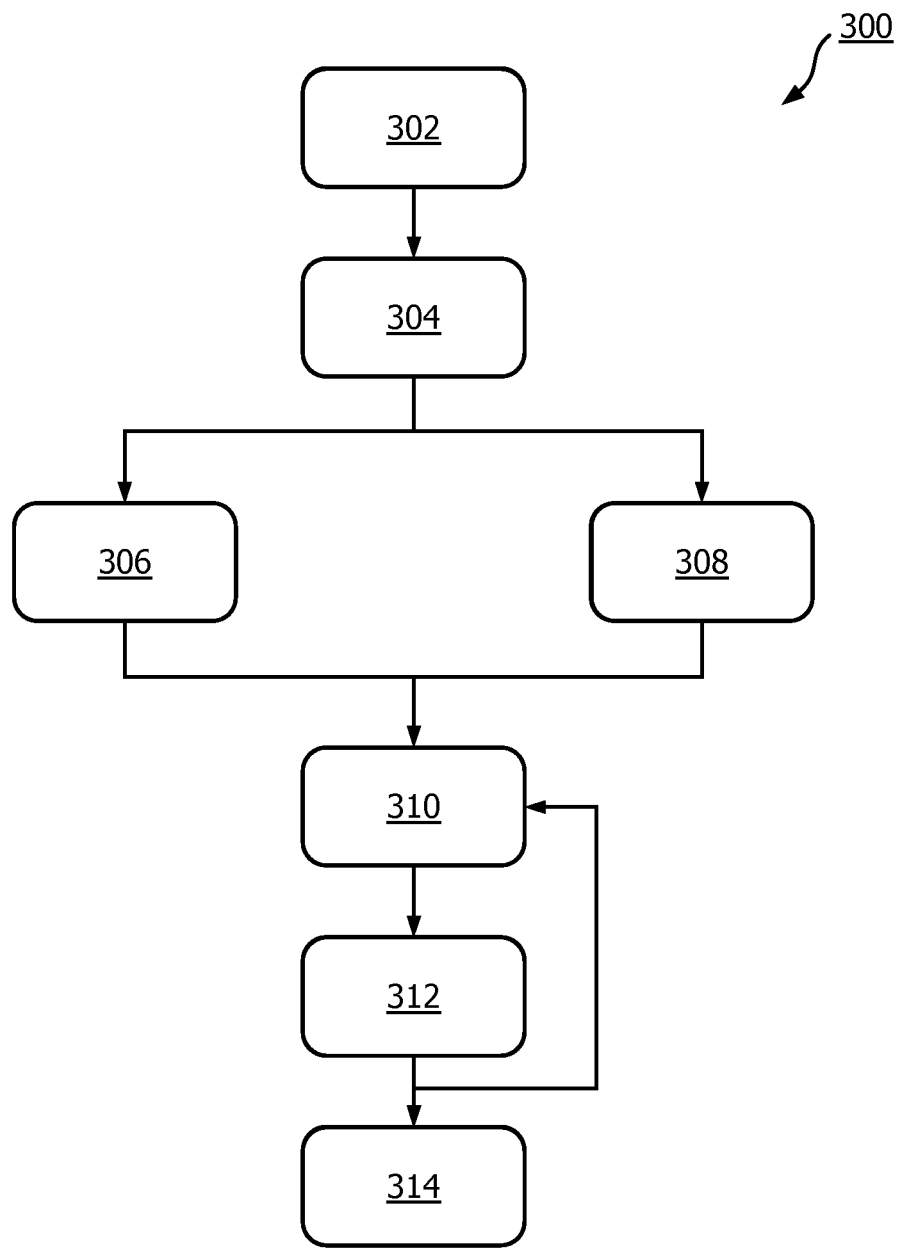
FIG. 3 shows a method of the invention.

FIG. 3 shows a method 300 of the invention.

In step 302, channel data is acquired by way of an ultrasonic probe. The channel data may comprise data relating to several observations of a region of interest.

In step 304, the channel data is beamformed. The beamforming may be performed by the image acquisition module 102, and more specifically by the beamforming delay module 170. The beamforming delay module may apply channel-specific delays to the channel data, thereby yielding the beamformed channel data 192.

In step 306, the beamformed channel data is used by the image acquisition module 102 to obtain a plurality of images 126-130. The plurality of images may each comprise a different viewing angle of a region of interest.

In parallel to step 306, in step 308, the beamformed channel data is used by the image content assessment module 154 to assess an image information metric. The image information metric may be a coherence metric, such as: a coherence factor; a covariance matrix; and, in most particularly in the case of RDT/IRDT focusing, a Wiener factor (although a Wiener factor may be used without RDT/IRDT focusing). These factors may be assessed as discussed above. Additionally, any combination of image metrics may be used to assess the beamformed channel data, such as coherence factor and Wiener factor or coherence factor and covariance matrix eigenvalue dominance. It should be noted that coherence factor and covariance matrix image metrics may be used in any scenario, regardless of whether RDT or IRDT focusing are employed. Alternatively, any other measure relating to the coherence of the signals of the channel may be assessed as the image information metric. The image information metrics are determined for image locations which spatially correspond to the images obtained in step 306.

In step 310, the assessed image information metric is used to determine a per-pixel weighting for each spatially corresponding pixel of an image.

In step 312, the per-pixel weightings are applied to each pixel of the image.

Steps 310 and 312 are repeated for each of the plurality of images.

In step 314, the compound ultrasound image 190 is generated based on the plurality of weighted pixels of the images. Image to image motion compensation, or plane compounding, may be applied to reduce motion artifacts in the final compound ultrasound image.

The final compound ultrasound image, $I_{compound}$, may be represented as:

$$I_{compound} = \Sigma_{i=1}^{N} w_i I_i$$

where: $w_i$ is the weight to be applied locally to the image, $I_i$. The images are compounded on a per-pixel basis, meaning that if the pixels of the images and weight maps are indexed x and y, then the equation becomes:

$$I_{compound_{x,y}} = \sum_{i=1}^{N} w_{i_{x,y}} I_{i_{x,y}}$$

As described above, the $w_{i_{x,y}}$ are derived from measure of coherence of the channel data, but may also be image-based.

In some cases, classification may be performed on the image information metric to determine whether the image information metric comprises a feature or an orientation of the region of interest. This classification may be performed over any spatial range of the image, for example, over a 124 pixel cube centered on the current pixel being assessed. If either a feature, such as a blood vessel, or an orientation are determined to be present in the image information metric, the pixel being assessed may be classified as important. This classification may then be taken into account during the determination of the per-pixel weightings.

For example, a weight of unity may be assigned to a pixel of one of the plurality of images that was as marked important and a weight of zero assigned to the remaining pixels of the remaining images. Alternatively, the weight determination may differentiate between found features and found orientations, giving, for example, priority to features. Another alternative is to split the weighted average between two pixels that were both marked as important. Also, classifying of importance may, instead of garnering the full weight of unity, be accorded a high weight such as 0.75, based on the image information metric analysis, affecting the weighting for the other spatially corresponding pixels.

Brightness maps may be generated form the plurality of images. For example, a maximum brightness value map may be constructed by selecting, for each pixel of the maximum brightness value map, the spatially corresponding pixel having the highest brightness value across the plurality of obtained images. Similarly, mean and minimum brightness maps may also be generated.

The maximum brightness value map constitutes an image that enhances the visibility of anisotropic structures; however, tissue smearing is maximized and contrast is deteriorated in this brightness map. In the mean brightness value map, the benefits of smoothing out speckle areas are realized. The minimum brightness value map depicts anisotropic structures poorly, but advantageously yields low brightness values inside cysts. It is beneficial to not enhance cyst areas, and not to bring sidelobe clutter into cysts. Additionally, a normalized image information metric map may also be generated.

The weightings may be determined as a function of the brightness maps, resulting in the following equation:

$$I_{compound} = w_{min} I_{min} + w_{mean} I_{mean} + w_{max} I_{max},$$

where $I_{min}$, $I_{mean}$, and $I_{max}$ are respectively the minimum, mean, and maximum brightness value maps over the images, respectively. As before, this may also be expressed in a pixel-wise form.

Exemplary implementations, based on the coherence factor (CF), are discussed below. More generally, based on the image information metric map, it is possible to determine a weight to assign to the minimum, mean and maximum spatially corresponding pixels to form a final compound ultrasound image, which contains all structures with maximum visibility and all cysts with maximum contrast.

Two possible implementations are described below, the first of which does not use the minimum brightness image and the second of which does. Using the minimum image increases image contrast by decreasing cyst clutter but may also result in unwanted signal reduction from real structures.

In a first implementation, a weighted average of the pixels is taken from the mean and maximum images. The three rules of this implementation are: 1) when the CF is above a given threshold $t_{max}$, select the pixel from the maximum image; 2) when the CF is below a given threshold $t_{min}$, select the pixel from the mean image; and 3) when the CF lies between the two threshold values, combine the two pixels. This can be formalized mathematically as follows:
Normalize CF between $t_{min}$ and $t_{max}$:

$$CF_{norm} = \max\left(0, \min\left(\frac{CF - t_{min}}{t_{max} - t_{min}}, 1\right)\right)$$

Determine the weights based on the normalized CF:

$$w_{mean} = 1 - CF_{norm}; w_{max} = CF_{norm}$$

Accordingly, instead of compounding the obtained images 126-130 directly, each compound pixel 191 is the weighted average of its counterpart in the mean brightness map and its counterpart in the maximum brightness map, those two counterpart pixels being weighted respectively by $w_{mean}$ and $w_{max}$. The weights may also have a quadratic, polynomial, or exponential expression.

The second implementation finds the weighted average of the minimum, mean and maximum images. In this case, the three rules are: 1) when the CF is above a given threshold $t_{max}$, select the pixel from the maximum image; 2) when the CF is below a given threshold $t_{min}$, select the pixel from the minimum image; and 3) in between, combine the pixels from the minimum, mean and maximum images, although some potential values of the CF will exclusively select the pixel from the mean image.

This can be formalized mathematically as follows:
Normalize CF between $t_{min}$ and $t_{max}$:

$$CF_{norm} = \max\left(0, \min\left(\frac{CF - t_{min}}{t_{max} - t_{min}}, 1\right)\right)$$

Determine the weights based on the normalized CF:

$$w_{min} = (1 - CF_{norm})^2; w_{max} = (CF_{norm})^2; w_{mean} = 1 - w_{min} - w_{max}$$

The weights may also have a linear, polynomial, or exponential expression.

Speckle artifacts introduced by the adaptive method can be removed, while retaining the contrast gains, as follows. The mean brightness value image is subtracted from the compound ultrasound image created in step S314. The resulting difference image is low-pass filtered and the low-pass-filtered image is added to the mean image to yield a despeckled image. The low-frequency image changes, such as larger structures and cysts, are consequently retained, while the higher frequency changes, such as speckle increase, are eliminated. The low-pass filter is realizable by convolution with, for example, a Gaussian or box kernel. A compound ultrasound image is now ready for displaying to a user.

Alternatively, with regard to speckle reduction, a programmable digital filter may be introduced to receive the beamformed data and separate the data of higher spatial frequencies, which contain the speckle signal, from the data of lower spatial frequencies. In this multi-scale approach, a multi-scale module passes on only the lower frequency data to the image content assessment module 154 for adaptive compounding. The higher frequency data are assigned equal compounding weights in the weight determination module 156. Furthermore, different metrics and different formulas for combining compounded sub-views into an compound image based on the metrics, may be advantageously applied at each subscale. For instance, low spatial frequencies may be more aggressively enhanced than higher spatial frequencies.

Optionally, the weights determined in a neighborhood of a spatially corresponding pixel 180a-180c may be combined, such as by averaging. A neighborhood could be a cluster of pixels, centered on the current pixel. In that case, compounding is performed with less granularity, i.e., neighborhood by neighborhood, instead of pixel by pixel. This may be employed in systems where processing power is a limiting factor. This also has the benefit of reducing the speckle variance of the weighted sub-images.

Figure 4:
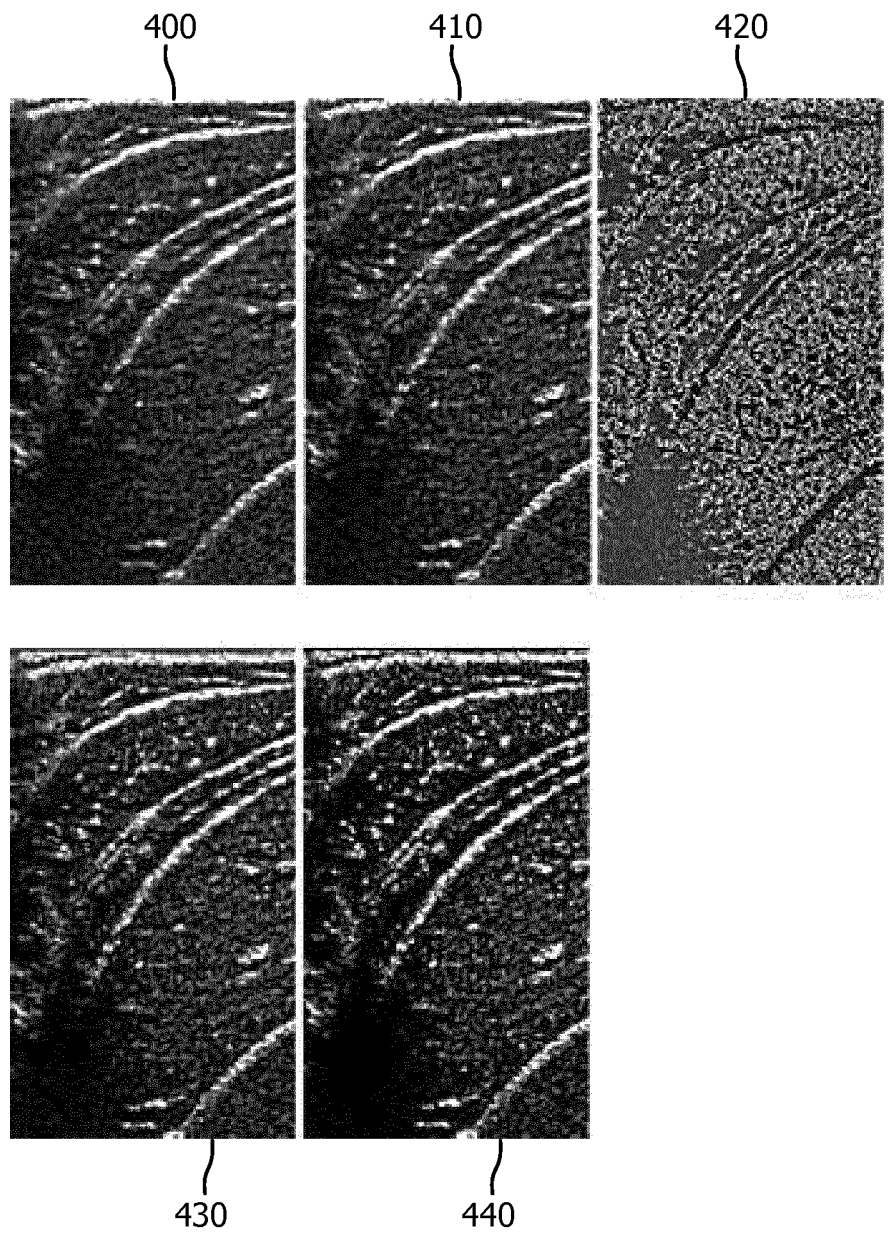
FIG. 4 shows a comparison between pixel brightness maps and a coherence factor map of an ultrasound image.

FIG. 4 shows a comparison between the mean and maximum brightness maps, the coherence factor map and the first and second weighting methods as described above.

Referring to FIG. 4, the first image 400 shows the mean brightness map, the second image 410 shows the max brightness map, the third image 420 shows the CF map, the fourth image 430 shows the mean-max adaptive image described in the first implementation above and the fifth image 440 shows the min-mean-max adaptive image described in the second implementation above.

The adaptive images present more contrast and sharpen the aspect of structures when compared to the mean and max brightness images. In addition, smearing of the fascia tissue into the surrounding muscle parenchyma is greatly reduced, especially when the minimum brightness image is used as well, as shown by the fifth image 440. Structures that are visible in the maximum brightness image but not the mean brightness image are still visible in the adaptive images, but with greater contrast than in the max image. The adaptive images tend to have more speckle than the mean image; however, this effect may be greatly reduced by spatial averaging/adaptive filtering of the coherence factor map as show in FIG. 5.

Figure 5:
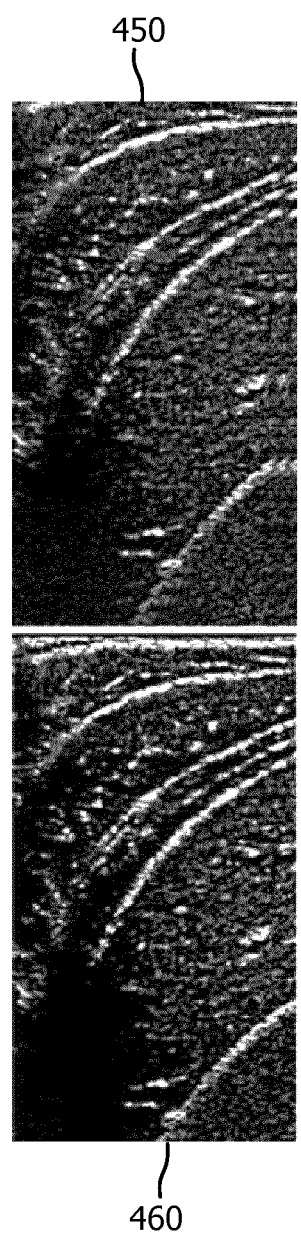
FIG. 5 shows the adaptive brightness maps of FIG. 4 after the application of a speckle reduction method.

Referring to FIG. 5, the first image shows the mean-max adaptive and the min-mean-max adaptive images after the application of the speckle reduction method described above as image 450 and 460, respectively. It is clear by comparison to the fourth 430 and fifth 440 images of FIG. 4 that the speckle, particularly in the darker regions, has been significantly reduced, thereby improving the contrast of the overall image.

While the invention has been illustrated and described in detail in the drawings and foregoing description, such illustration and description are to be considered illustrative or exemplary and not restrictive; the invention is not limited to the disclosed embodiments.

For example, within the intended scope of what is proposed herein is a computer readable medium, as described below, such as an integrated circuit that embodies a computer program having instructions executable for performing the process represented in FIG. 3. The processing is implementable by any combination of software, hardware and firmware.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for generating a compound ultrasound image, the method comprising:
   acquiring channel data;
   beamforming the channel data;
   in parallel:
      obtaining a plurality of images from the beamformed channel data, each image comprising a plurality of pixels, of a region of interest; and
      assessing an image information metric of the beamformed channel data, wherein the image information metric corresponds to each pixel of the plurality of images; and
   for each image of the plurality of images:
      determining a per-pixel weighting for each pixel of the plurality of pixels based on the assessment of the image information metric; and
      applying the per-pixel weighting to each pixel of the plurality of pixels; and
   generating a compound ultrasound image based on the plurality of weighted pixels of the plurality of images.

2. A method as claimed in claim 1, wherein the plurality of pixels are volumetric pixels.

3. A method as claimed in claim 1, wherein each image of the plurality of images comprises a viewing angle of the region of interest, wherein the viewing angle of each image is different.

4. A method as claimed in claim 1, wherein the image information metric comprises at least one of a feature and an orientation.

5. A method as claimed in claim 1, wherein the assessing of the image information metric comprises assessing a coherence metric of the beamformed channel data.

6. A method as claimed in claim 5, wherein the coherence metric comprises at least one of: a coherence factor; a dominance of an eigenvalue of a covariance matrix; and a Wiener factor.

7. A method as claimed in claim 1, wherein the generation of the compound ultrasound image comprises performing at least one of: spatial; temporal; or frequency compounding on the plurality of weighted pixels.

8. A method as claimed in claim 1, wherein the generation of the compound ultrasound image comprises at least one of retrospective dynamic transmit (RDT) focusing and incoherent RDT focusing.

9. A method as claimed in claim 1, wherein the generation of the compound ultrasound image is performed in a multi-scale fashion.

10. A method as claimed in claim 1, wherein the method further comprises assigning brightness values to the plurality of pixels of each image based on the assessment of the image information metric.

11. A method as claimed in claim 10, wherein the determining of the weighting for each pixel is based on at least one of a maximum brightness value; a mean brightness value; and
   a minimum brightness value of the plurality of pixels across the plurality of images.

12. A method as claimed in claim 11, wherein the method further comprises:
   generating a mean brightness value image based on the mean brightness value of the plurality of pixels across the plurality of images;
   subtracting the mean brightness value image from the compound ultrasound image, thereby generating a difference image;
   applying a low pass filter to the difference image; and
   summing the mean brightness value image and the difference image, thereby generating a speckle filtered compound ultrasound image.

13. A computer program stored on a non-transitory medium, the computer program comprising computer program code means which is adapted, when said computer program is run on a computer, to implement the method of claim 1.

14. A system for generating a compound ultrasound image, the system comprising:
   ultrasound probe, adapted to acquire channel data;
   beamformer, adapted to apply beamforming to the channel data;
   a controller adapted to:
      in parallel:
         obtain a plurality of images from the beamformed channel data, each image comprising a plurality of pixels, of a region of interest; and
         assess an image information metric of the beamformed channel data, wherein the image information metric corresponds to each pixel of the plurality of images; and
      for each image of the plurality of images:
         determine a per-pixel weighting for each pixel of the plurality of pixels based on the assessment of the image information metric; and
         apply the per-pixel weighting to each pixel of the plurality of pixels; and
   a pixel compounder, adapted to generate a compound ultrasound image based on the plurality of weighted pixels of the plurality of images.

15. A system as claimed in claim 14, wherein the ultrasound probe comprises an electronic steering unit adapted to alter a viewing angle of the ultrasound probe.

16. A system as claimed in claim 14, wherein, to obtain the plurality of images, the controller is adapted to:
   perform at least one of envelope detection, log compression, scan conversion, or spatial registration using the beamformed channel data in parallel with the assessment of the image information metric.

17. A method as claimed in claim 1, wherein, the obtaining the plurality of images comprises:
   performing at least one of envelope detection, log compression, scan conversion, or spatial registration using the beamformed channel data in parallel with the assessment of the image information metric.

18. A system as claimed in claim 14, wherein:

the controller comprises a first processing pathway and a different, second processing pathway in parallel with the first processing pathway, and to obtain the plurality of images and assess the image information metric in parallel, the controller is adapted to:

obtain the plurality of images using the first processing pathway; and assess the image information metric using the second processing pathway.

* * * * *